(12) United States Patent
Tsujii (10) Patent No.: US 7,082,184 B2
(45) Date of Patent: Jul. 25, 2006

(54) TOMOSYNTHESIS IMAGING METHOD AND APPARATUS FOR SUPPRESSING UNNECESSARY IRRADIATION

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 28 days.

(21) Appl. No.: 10/853,986

(22) Filed: May 26, 2004

(65) Prior Publication Data

US 2004/0240605 A1 Dec. 2, 2004

(30) Foreign Application Priority Data

May 27, 2003 (JP) ............................. 2003-149566

(51) Int. Cl.
*A61B 6/02* (2006.01)
(52) U.S. Cl. .................................................. 378/21
(58) Field of Classification Search .................. 378/21, 378/22, 23, 24, 25, 26, 27, 205
See application file for complete search history.

(56) References Cited

U.S. PATENT DOCUMENTS 4,581,535 A * 4/1986 Komaki et al. ............... 378/23
5,995,581 A * 11/1999 Ozaki ............................ 378/20
2004/0081281 A1 * 4/2004 Fadler et al. ................ 378/205

FOREIGN PATENT DOCUMENTS

JP 57-203430 12/1982
JP 6-217969 8/1994

OTHER PUBLICATIONS

English Abstract for Japanese Laid-Open Patent Application No. 6-217969.

\* cited by examiner

*Primary Examiner*—Edward J. Glick
*Assistant Examiner*—Chih-Cheng Glen Kao
(74) *Attorney, Agent, or Firm*—Morgan & Finnegan, LLP

(57) ABSTRACT

In the first process, imaging is performed to obtain a tomosynthesis surface setting image. In X-ray tomosynthesis imaging, a subject (9) to be imaged is imaged while laid down on a bed table (25). An X-ray generator (13) and X-ray image detector (19) are positioned to laterally image the subject (9) in this lying state. In the second process, tomosynthesis surface information such as the position, range, and shape of a tomosynthesis surface is set. In the third process, a path, tomosynthesis angle, and fan angle are calculated to obtain a necessary amount of set tomosynthesis surface information, thereby executing data acquisition.

6 Claims, 10 Drawing Sheets

IMAGING FOR TOMOSYNTHESIS
SURFACE SETTING IMAGE

FIG. 1A

TOMOSYNTHESIS SURFACE

TOMOSYNTHESIS SURFACE SETTING

FIG. 1B

IMAGING FOR TOMOSYNTHESIS SURFACE SETTING IMAGE

FIG. 1C

TOMOSYNTHESIS IMAGING

TOMOSYNTHESIS IMAGING METHOD AND APPARATUS FOR SUPPRESSING UNNECESSARY IRRADIATION

FIELD OF THE INVENTION

The present invention relates to an imaging apparatus such as an X-ray digital tomosynthesis imaging apparatus using a flat panel and, more particularly, to an imaging method which suppresses unnecessary irradiation with X-rays by controlling the path of an X-ray generator in tomosynthesis imaging of a subject to be imaged.

BACKGROUND OF THE INVENTION

The X-ray tomosynthesis imaging apparatus disclosed in Japanese Patent Laid-Open No. 57-203430 can reconstruct a plurality of cross sections by acquiring imaged data obtained by one tomosynthesis imaging operation. More specifically, there are disclosed an X-ray generator, a two-dimensional detector, a driving mechanism which moves the X-ray generator and two-dimensional detector in relatively opposite directions, a position detector which detects the movement positions of the generator and detector, a storage device which stores images obtained every relative movement of the above components in association with the respective positions, and a device which computes the storage position of image information at an arbitrary point on a subject to be imaged in the depth direction, and calculates an image display signal.

In CT, in some cases, a scanogram (a projection image which provides an overall view along the body axis direction) which is used to determine a cross section position before imaging of a CT cross section is obtained by imaging in advance, and a cross section position where data acquisition is to be performed is set on the basis of the scanogram. In CT based on the recent spiral scheme, however, a cross section position is not finely set in data acquisition, and a calculated cross section is designated only in calculation of a cross section image.

Note that in this case, the terms "cross section" and "tomosynthesis" are distinctively used. The term "cross section" means a surface like that imaged in CT, which is perpendicular to the body axis of a human body. The term "tomosynthesis" means a surface like that imaged by a conventional analog tomosynthesis imaging apparatus, which is parallel to the body axis of a human body.

Japanese Patent Laid-Open No. 6-217969 discloses a technique of limiting an X-ray irradiation range to only a film surface by controlling an X-ray stop in accordance with a tomosynthesis angle, thereby reducing scattered radiation. This technique is based on consideration of a tomosynthesis angle $\xi$ and a fan angle $\theta$ of an X-ray generator in acquiring projection data with respect to a given tomosynthesis surface p in a subject to be imaged in a conventional analog tomosynthesis imaging apparatus.

More specifically, according to this reference, as the tomosynthesis angle $\xi$ increases, the fan angle $\theta$ necessary for the formation of the tomosynthesis surface p decreases.

The above tomosynthesis imaging apparatus is used less these days in the clinical field because of CT. However, with advances in digital tomosynthesis imaging techniques, multiple tomosyntheses can be reconstructed by one tomosynthesis imaging operation, thus realizing higher imaging throughput and smaller exposure dose than CT. For such reasons, attention has been given to the tomosynthesis imaging apparatus again.

It is therefore required for a tomosynthesis imaging apparatus as well as a CT to obtain in advance a setting image by imaging, which is used to arbitrarily set a tomosynthesis surface to be tomosynthetically imaged.

More specifically, it is required to improve the efficiency of imaging and subsequent diagnosis by allowing arbitrary setting of the position, range, shape, and the like of a target tomosynthesis surface before tomosynthesis imaging operation, and to reduce the exposure dose of a subject to be examined by irradiating the subject with only radiation necessary for imaging.

SUMMARY OF THE INVENTION

The present invention has been made in consideration of the above problems, and has as its object to provide an imaging method and apparatus which can improve the efficiency of imaging and subsequence diagnosis by allowing arbitrary setting of the position, range, shape, and the like of a target tomosynthesis surface before tomosynthesis imaging operation, and reduce the exposure dose of a human body as a subject to be examined.

In order to solve the above problems and achieve the above object, according to the present invention, there is provided an imaging apparatus which takes a transmission image of a subject to be imaged by imaging using X-rays, comprising setting image obtaining means for obtaining at least one tomosynthesis surface setting image before execution of tomosynthesis imaging of the subject, tomosynthesis surface setting means for setting a tomosynthesis surface on the basis of the setting image, and tomosynthesis condition setting means for setting a tomosynthesis imaging condition on the basis of the set tomosynthesis surface.

According to the present invention, there is provided an imaging method which takes a transmission image of a subject to be imaged by imaging using X-rays, comprising a setting image obtaining step of obtaining at least one tomosynthesis surface setting image before execution of tomosynthesis imaging of the subject, a tomosynthesis surface setting step of setting a tomosynthesis surface on the basis of the setting image, and a tomosynthesis condition setting step of setting a tomosynthesis imaging condition on the basis of the set tomosynthesis surface.

According to the present invention, there is provided a program for taking a transmission image of a subject to be imaged by imaging using X-rays, the program causing a computer to execute a setting image obtaining function for obtaining at least one tomosynthesis surface setting image before execution of tomosynthesis imaging of the subject, a tomosynthesis surface setting function for setting a tomosynthesis surface on the basis of the setting image, and a tomosynthesis condition setting function for setting a tomosynthesis imaging condition on the basis of the set tomosynthesis surface.

According to the present invention, there is provided a computer-readable storage medium which stores a program for taking a transmission image of a subject to be imaged by imaging using X-rays, the program causing a computer to execute a setting image obtaining function for obtaining at least one tomosynthesis surface setting image before execution of tomosynthesis imaging of the subject, a tomosynthesis surface setting function for setting a tomosynthesis surface on the basis of the setting image, and a tomosynthesis condition setting function for setting a tomosynthesis imaging condition on the basis of the set tomosynthesis surface.

The setting image is preferably obtained by imaging along a direction substantially perpendicular to a moving direction of an X-ray source.

The tomosynthesis surface preferably comprises a surface extending along a body axis of the subject.

The tomosynthesis surface setting means (step, function) preferably can set at least one of a position, a range, and a shape of a tomosynthesis surface.

The shape of the tomosynthesis surface preferably includes a flat surface and a curved surface.

The tomosynthesis imaging condition preferably includes at least one of an X-ray stop condition, an X-ray driving voltage, an X-ray driving current, and a pivoting scanning condition for the X-ray source.

The setting image preferably comprises an image taken from at least two orthogonal directions.

As described above, according to the present invention, the position, range, shape, and the like of a target tomosynthesis surface can be arbitrarily set before tomosynthesis imaging operation to improve the efficiency of imaging and subsequent diagnosis while optimizing image quality, and the exposure dose of a human body as a subject to be examined can be reduced.

Other objects and advantages besides those discussed above shall be apparent to those skilled in the art from the description of a preferred embodiment of the invention, which follows. In the description, reference is made to accompanying drawings, which form a part thereof, and which illustrate an example of the invention. Such example, however, is not exhaustive of the various embodiments of the invention, and therefore reference is made to the claims, which follow the description for determining the scope of the invention.

DETAILED DESCRIPTION OF THE PREFERRED EMBODIMENTS

The preferred embodiments of the present invention will be described below with reference to the accompanying drawings.

An imaging method and apparatus of the present invention can acquire a projection (setting) image which allows setting of the position, range, and shape of a tomosynthesis surface (to be also referred to as a slice), and control an X-ray generator on the basis of the position, range, and shape of the tomosynthesis surface which are set on the basis of the projection image.

In this case, controlling the X-ray generator is mainly controlling the movement of an X-ray tube (the path of an X-ray source, e.g., translational scanning), tomosynthesis angle $\xi$, and fan angle $\theta$. However, the present invention is not limited to this, and a tube current or voltage may be controlled.

Figure 1A:
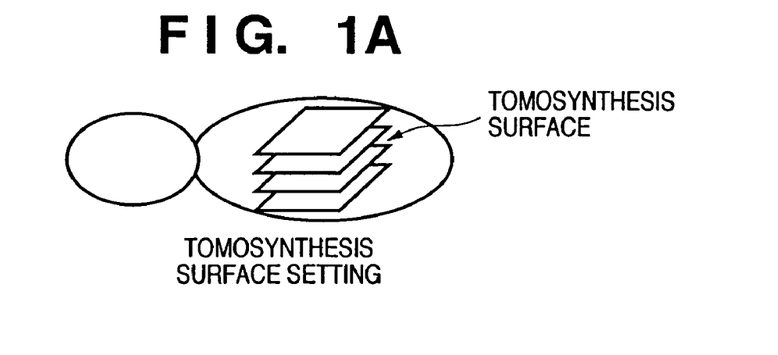
FIGS. 1A to 1C are views schematically showing a tomosynthesis imaging method of the present invention.
Figure 1B:
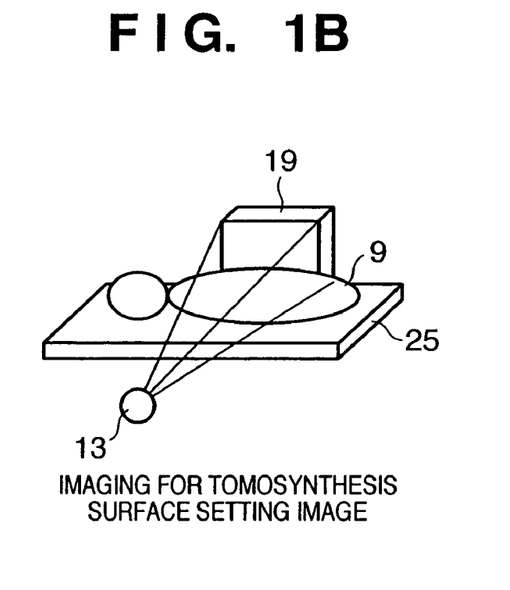
Figure 1C:
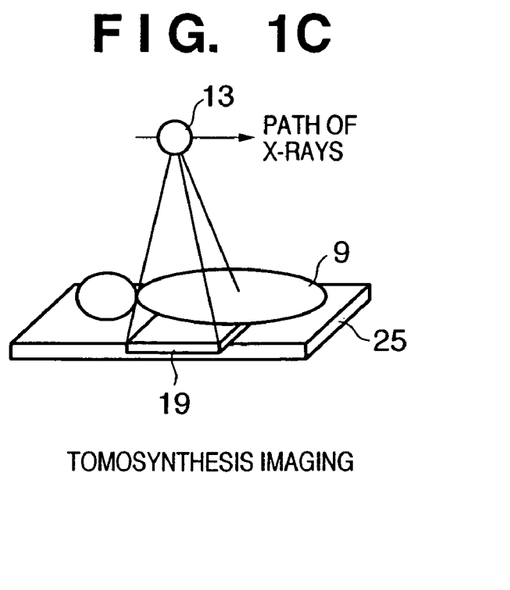

FIGS. 1A to 1C schematically show a tomosynthesis imaging method according to the present invention. In the first process (FIG. 1A), imaging is performed to obtain a tomosynthesis surface setting image.

X-ray tomosynthesis imaging is generally performed while a subject to be examined (e.g., a subject to be examined or a patient) 9 is lying down on a bed table 25 (lying position). An X-ray generator (X-ray tube) 13 and X-ray image detector 19 are positioned to image the subject 9 at this lying position. This operation can be regarded as lateral imaging with respect to the subject 9.

Although the case shown in FIGS. 1A to 1C is based on the assumption that only one lateral image of the subject 9 is used, the number of images to be used is not limited to one. Using a plurality of lateral images makes it possible to three-dimensionally set the position of a tomosynthesis surface in the second process.

In the second process (FIG. 1B), tomosynthesis surface information is set. More specifically, this tomosynthesis surface information includes at least the position, range, or shape of a tomosynthesis surface. In addition, for example, the thickness of a tomosynthesis surface (the slice thickness of a cross section in CT) used for the calculation of a tomosynthesis surface can be set.

Although setting this slice thickness does not greatly influence data acquisition conditions, the averaging range of data used for the calculation of a tomosynthesis surface is set.

Tomosynthesis surface information to be set is equivalent to a tomosynthesis position and cutting pitch in the prior art. The embodiment of the present invention, however, is not limited to conventional setting operation of designating the number of tomosynthesis surfaces after designating a cutting pitch, and allows setting of the location, size, and shape (a flat surface or a curved surface conforming to a given organ) of a tomosynthesis surface.

If only one setting image is to be used in the second process, the range of a tomosynthesis surface viewed from the front direction of the subject 9 cannot be designated because there is no tomosynthesis surface information in the front direction. In normal use, however, no problem arises because a technician (a doctor in the department of radiology, a radiographer, or the like) manually sets an X-ray irradiation range viewed from the front of the subject before imaging operation.

However, depending on a path (moving) method for an X-ray tube used for imaging operation (a linear path, elliptic path, spiral path, or the like), the fan angle $\theta$ cannot be accurately controlled. In addition, if the above tomosynthesis surfaces to be set vary in location and size, setting cannot be done.

Under the circumstances, as described above, the use of a plurality of setting frames may be taken into consideration.

More specifically, a plurality of images are stereoscopically displayed to provide a three-dimensional space for the technician, thereby allowing setting operation.

In the third process (FIG. 1C), a path, tomosynthesis angle, and fan angle are calculated to execute data acquisition, on the basis of the tomosynthesis surface information set in the second process, such that a necessary amount of information on the set tomosynthesis surface is obtained.

After the above data acquisition, each tomosynthesis surface is calculated by a calculation method such as a back-projection method, and the resultant information is displayed on a display device such as a display.

First Embodiment

Figure 2:
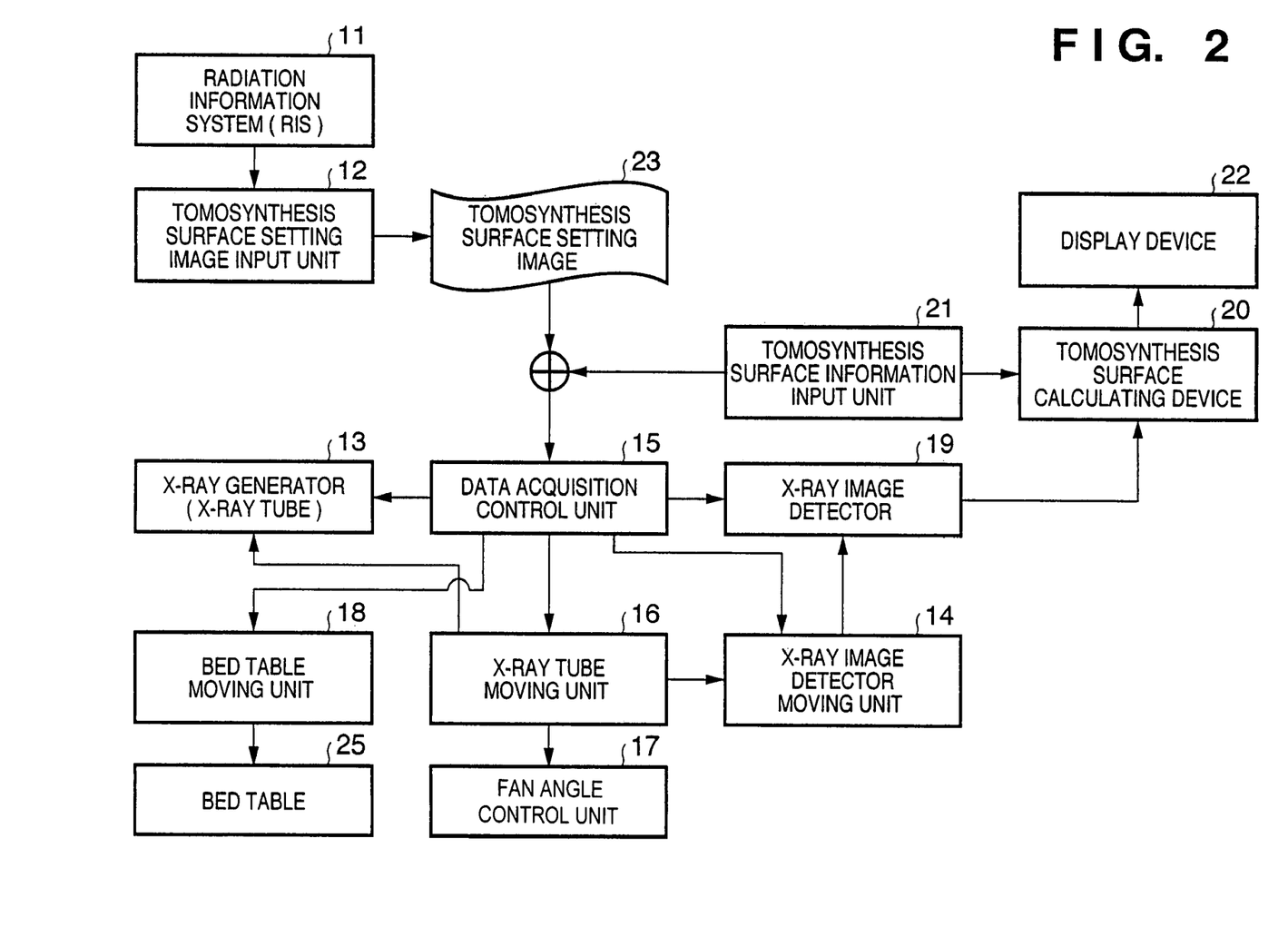
FIG. 2 is a block diagram of an X-ray tomosynthesis imaging apparatus according to the first embodiment.

FIG. 2 is a block diagram of a tomosynthesis imaging apparatus according to the first embodiment of the present invention. A request for tomosynthesis imaging is sometimes directly input to the X-ray tomosynthesis imaging apparatus, but is generally input from a radiation information system (RIS) 11. Information from the radiation information system 11 includes the unique information of a subject subjected to tomosynthesis imaging in addition to the body part information of the subject. The body part information of the subject is body part information about the head portion, chest portion, abdominal portion, or the like.

X-ray conditions are set by referring to a preset X-ray condition table (not shown) on the basis of the body part information, the unique information (height, age, and weight), and the like.

At the same time when the above X-ray conditions are set, the X-ray generator 13 and X-ray image detector 19 are moved to an imaging position to acquire a tomosynthesis surface setting image 23 corresponding to a region to be imaged from a tomosynthesis surface setting image input unit 12. This movement can be automatically done on the basis of the unique information of the subject, but may be manually done by a technician.

The tomosynthesis surface setting image 23 is generally obtained as a lateral image by imaging, and is an image of a surface perpendicular to a tomosynthesis image.

This tomosynthesis surface setting image 23 is displayed on a display device 22, and tomosynthesis surfaces are set on the basis of the tomosynthesis surface setting image 23.

Figure 3:
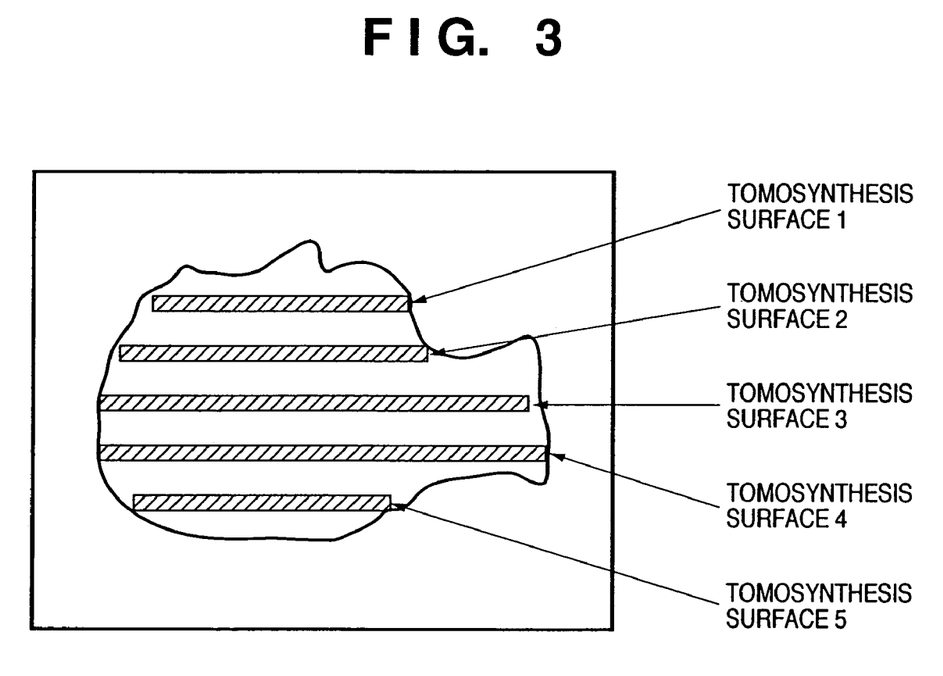
FIG. 3 is a view showing a set example of tomosynthesis surfaces (flat surfaces) using a setting image.

FIG. 3 shows the tomosynthesis surface setting image 23 and the tomosynthesis surface information input from a tomosynthesis surface information input unit 21 with the head portion being a subject to be imaged.

In this case, five tomosynthesis surfaces having different sizes are set.

Figure 4:
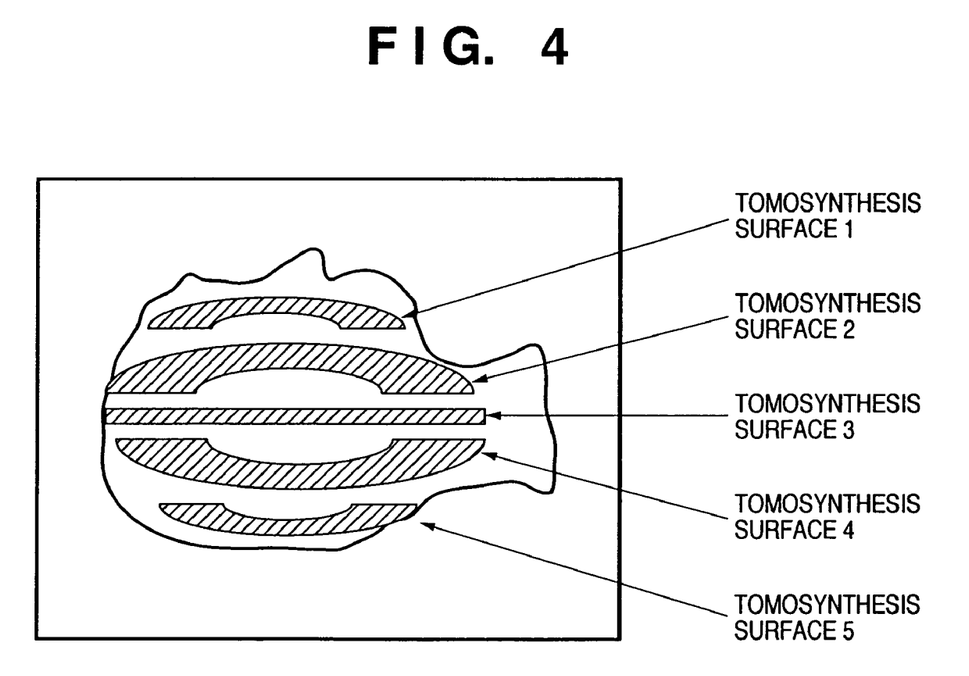
FIG. 4 is a view showing a set example of tomosynthesis surfaces (curved surfaces) using a setting image.

In the case shown in FIG. 3, the set tomosynthesis surfaces are flat. However, they need not be limited to flat surfaces, and arbitrary surfaces such as curved surfaces can be set. FIG. 4 shows a case wherein tomosynthesis surfaces are curved surfaces.

As shown in FIG. 2, on the basis of the tomosynthesis surface information set by the tomosynthesis surface information input unit 21, a data acquisition control unit 15 calculates control data for driving the X-ray generator 13, X-ray image detector 19, and bed table 25 so as to acquire data necessary for the reconstruction of the above tomosynthesis surfaces. An X-ray tube moving unit 16, X-ray image detector moving unit 14, and bed table moving unit 18 are controlled on the basis of the control data. Data acquisition is then executed in accordance with the data acquisition plan determined by the data acquisition control unit 15.

In acquiring data, the position of the bed table at the time of acquisition of the setting image 23 is used as a reference. This operation is therefore based on the assumption that the subject does not move between two imaging operations.

X-ray transmission data is detected by the X-ray image detector 19 and back-projected on a tomosynthesis surface designated on the basis of geometrical information of the acquired data. The reconstructed tomosynthesis surface by a tomosynthesis surface calculating device 20 is displayed on the display device 22, thus terminating the imaging operation.

A method of controlling the X-ray generator 13, the X-ray image detector 19, the bed table 25, the X-ray tube moving unit 16, the X-ray image detector moving unit 14, the bed table moving unit 18, and a fan angle control unit 17 on the basis of tomosynthesis surface information will be described next.

Figure 5:
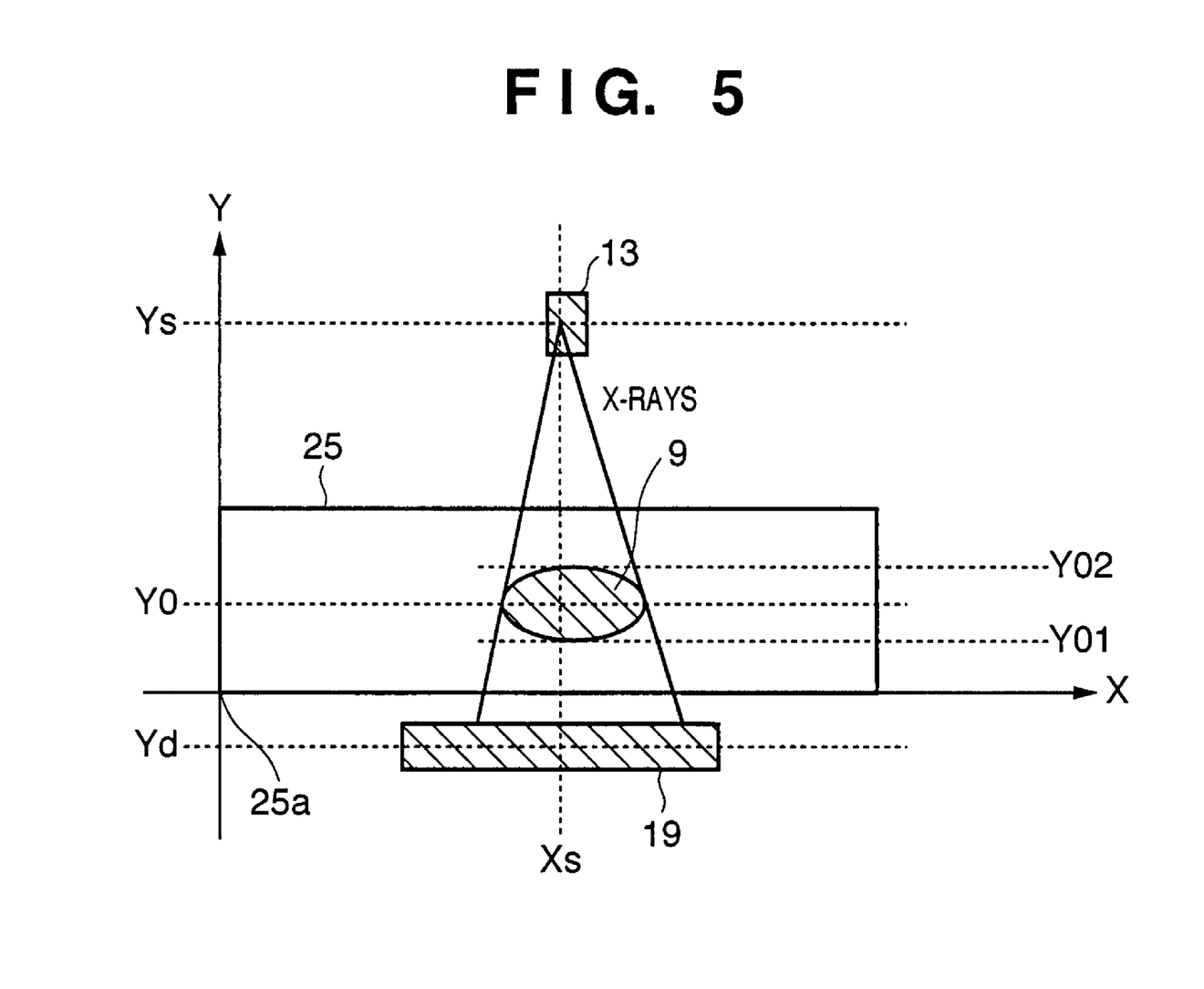
FIG. 5 is a plan view of an imaging system for a setting image.
Figure 6:
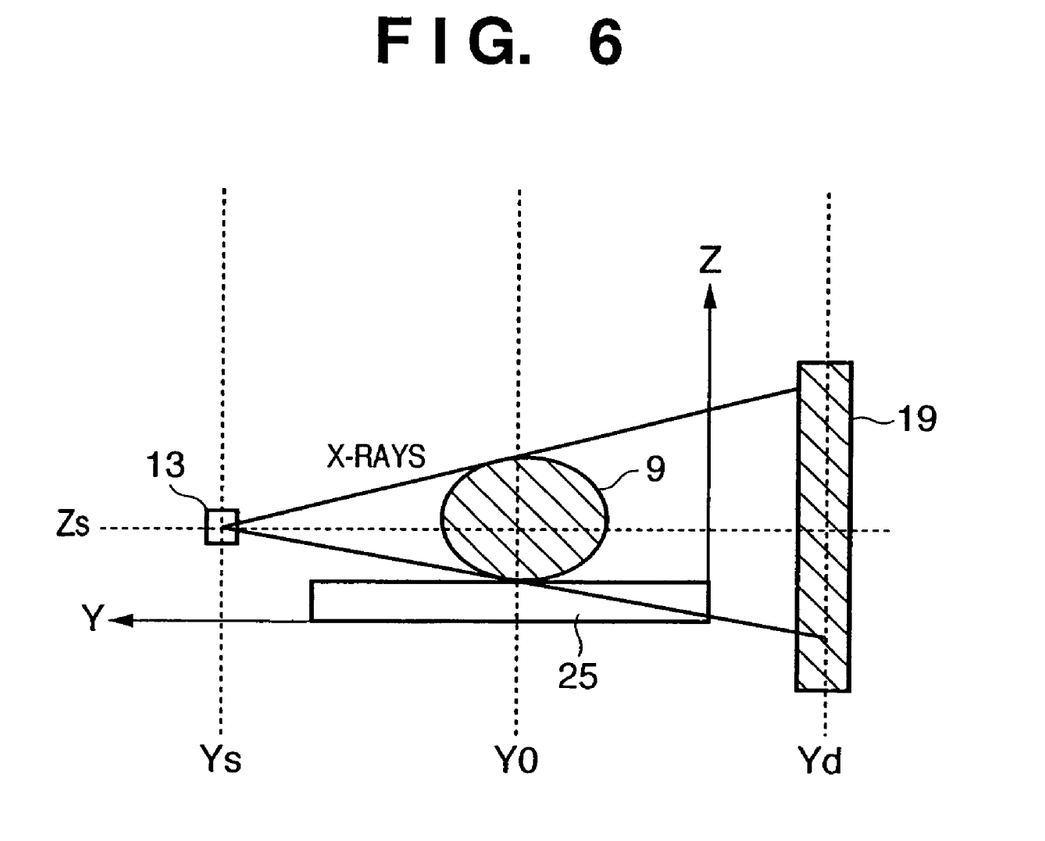
FIG. 6 is a side view of the imaging system for a setting image when viewed from the minus direction of the X-axis.

FIG. 5 is a plan view of a coordinate system set when a setting image is obtained by imaging. FIG. 6 is a side view taken from the minus direction of the X-axis in FIG. 5. For the sake of easy explanation, assume that data acquisition is performed while the bed table 25 is fixed (the subject 9 is also fixed on the table), and the X-ray generator 13 and X-ray image detector 19 are moved. Therefore, the three-dimensional coordinate system shown in FIG. 5 is determined with reference to one corner portion 25a of the bed table 25.

The X-ray focus is set to coordinates (Xs, Ys, Zs) to position in the center of the X-ray image detector 19. The subject 9 is set in the middle (−, Y0, −) of the bed table 25. If the center of the X-ray image detector 19 is placed at coordinates (Xs, Yd, Zs), an image of the subject 9 is formed on the X-ray image detector 19 at an enlargement ratio of (Ys−Yd)/(Ys−Y0).

Figure 7:
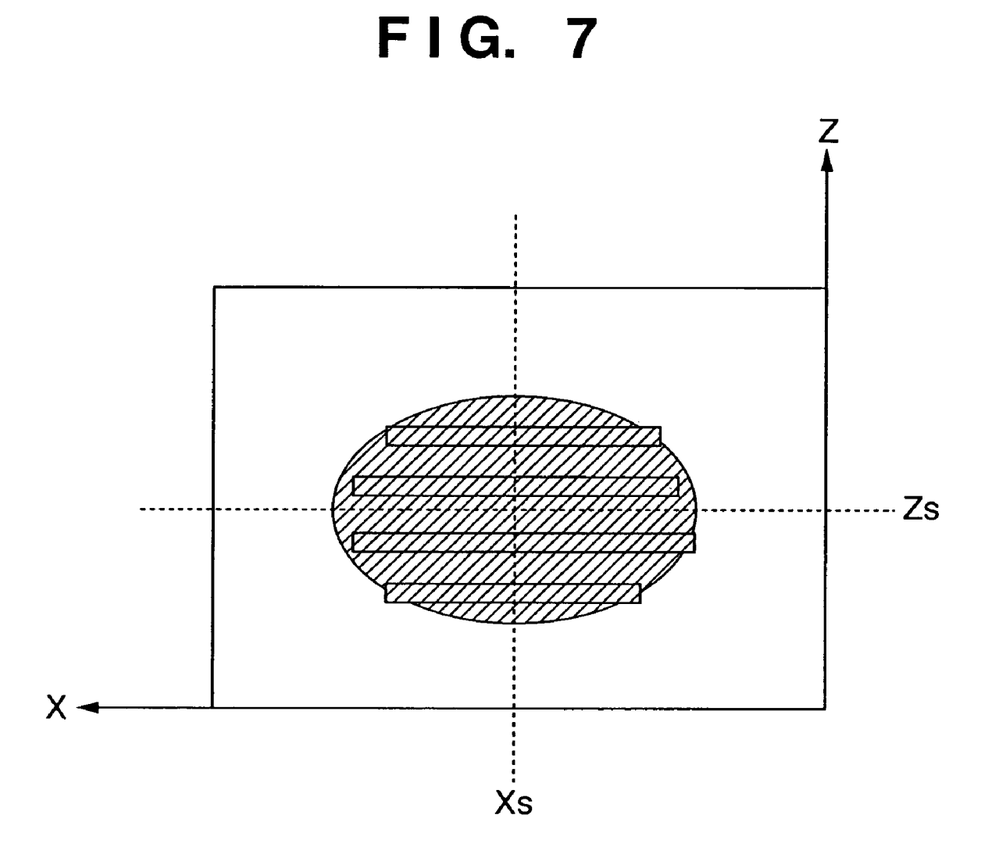
FIG. 7 is a view showing a tomosynthesis surface setting example.

FIG. 7 shows an example of the image obtained by such imaging operation. A tomosynthesis surface is set for this image in the manner shown in FIG. 7. It is assumed that the set tomosynthesis surface is rectangular or circular. Even if the tomosynthesis surface is limited to a rectangular shape, the length information of the subject 9 in the Y direction is omitted, as described above. For this reason, the X-ray stop state set by the technician at the time of tomosynthesis imaging is used as stop setting information in the Y direction.

The usage pattern of this stop setting information in the Y direction varies depending on the path selected. That is, when a linear path is selected, there is no need to change the stop information set by the technician during tomosynthesis imaging, and it suffices if the stop setting in the Y direction remains the same.

On the other hand, when a circular or elliptic path is selected, since a tomosynthesis angle is produced in the Y direction, scattered radiation can be optimally controlled by changing the stop in the Y direction in accordance with the angle.

When, therefore, a circular or elliptic path is selected, the stop information set by the technician is used as stop setting information in the Y direction.

FIG. 5 shows an example of the stop setting information in the Y direction which is set by the technician. Note that FIG. 5 is a view showing imaging operation for a setting image, but is not a view showing imaging operation for tomosynthesis data. The setting information (from Y01 to Y02) in the Y direction represents the effective width of the subject 9 in the Y direction for the sake of convenience.

Figure 8:
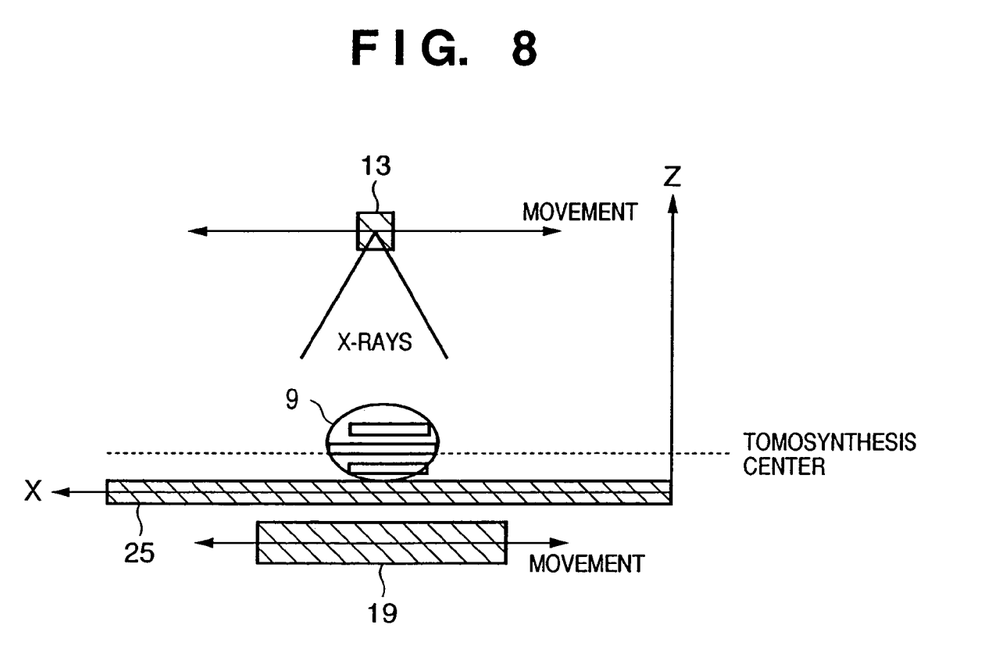
FIG. 8 is a view showing data acquisition conditions for tomosynthesis surface setting.

FIG. 8 shows the tomosynthesis surfaces set in FIG. 7, superimposed on an actual imaging system. This superimposition is made in consideration of the above enlargement ratio. In this case, the center of a tomosynthesis surface is preferably set on a tomosynthesis surface of the set tomosynthesis surfaces which has the largest area, in terms of efficiency. To be precise, in order to reduce the exposure dose, the center of a tomosynthesis surface is preferably set such that the cumulative value of fan angles θ at a plurality of imaging positions where data are acquired becomes minimized in calculation of the fan angles θ.

In general, however, since this requires complicated calculations, the center of a tomosynthesis surface is set on the largest tomosynthesis surface or on a cross section in the center of the set tomosynthesis surface.

The relationship between a tomosynthesis surface, the tomosynthesis angle ξ, the fan angle θ will be described next.

An important point is that the fan angle θ is obtained so as to set sufficient data for the plurality of set tomosynthesis surfaces. That is, as shown in FIG. 9, when tomosynthesis surfaces are set within a limited range in the subject, a portion of the subject is irradiated with X-rays.

Figure 9:
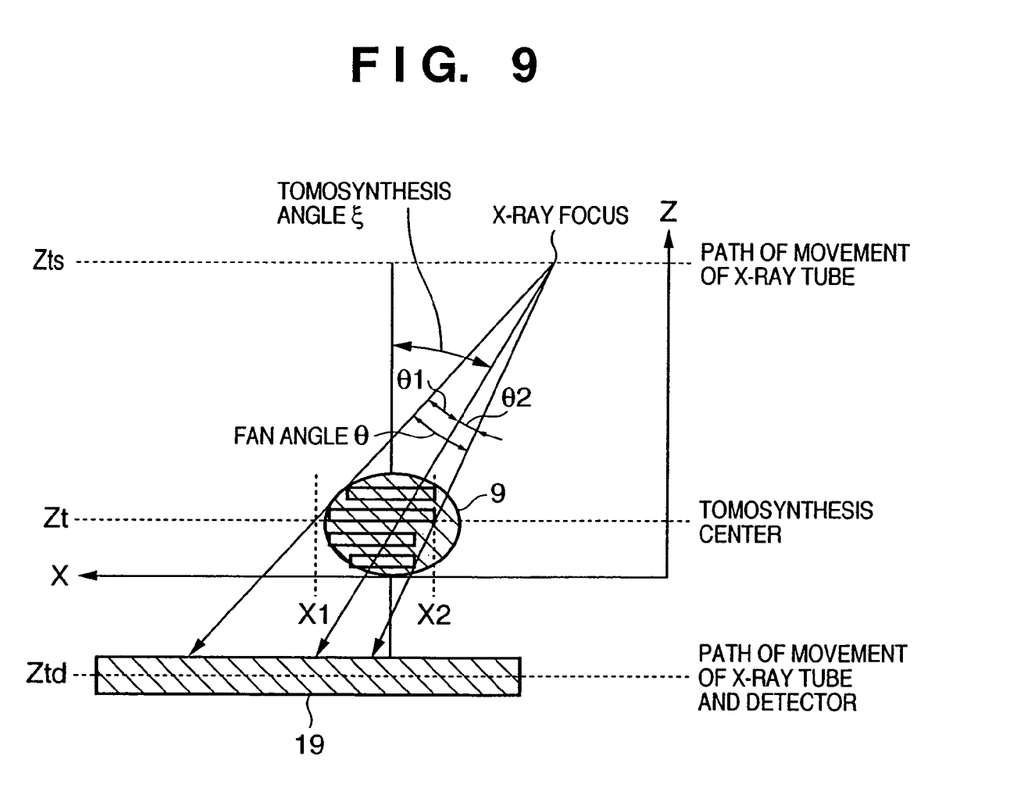
FIG. 9 is a view for explaining a method of calculating a fan angle.

FIG. 9 shows an example of the fan angle θ in the X direction. Letting ξ be a tomosynthesis angle, Zt, Zts, and Ztd be a tomosynthesis center, a focus, and the Z-coordinate of the detector, respectively, and X1 and X2 be two points where an X-ray beam enveloping a plurality of tomosynthesis surfaces passes through the tomosynthesis center, when fan angle θ=θ1+θ2, we have:

$$(Xs-X2)/L = \tan\theta - \tan(\xi-\theta2) \quad (1)$$

$$-(X1-Xs)/L = \tan\theta - \tan(\xi+\theta1) \quad (2)$$

where L=(Ztd−Zt).

The fan angle θ can be calculated from equations (1) and (2).

As is obvious from this, the fan angle θ is a function of the two points X1 and X2 and the tomosynthesis angle ξ which is calculated to envelop all the tomosynthesis surfaces. Although not shown, since θ1 and θ2 have their own limits, the X-ray tube needs to be swingable (the X-ray tube itself is pivoted and scanned while its movement along the path is fixed (or moved), in order to realize fan angle θ (=θ1+θ2). In general, the X-ray tube needs to be swingable in a region where the tomosynthesis angle ξ is large.

The above description is limited to only a case wherein the path of the X-ray tube is linear at the time of tomosynthesis imaging. However, the same calculation method as described above is used even if the path is a circular or elliptic path. Note that as tomosynthesis surface information in the Y direction on a circular or elliptic path, the X-ray stop information set by the technician is used except when a plurality of setting images are to be obtained by imaging to be described in the second embodiment.

As described above, optimal X-ray stop conditions can be calculated so as to envelop set tomosynthesis surfaces on the basis of a setting image for setting tomosynthesis surfaces. On the other hand, an X-ray irradiation amount (a combination of a tube voltage and a tube current) required to obtain a sufficient S/N ratio by analyzing the setting image.

Second Embodiment

The first embodiment has exemplified the case wherein only one tomosynthesis surface setting image is used. However, data acquisition conditions can be set more strictly by using a plurality of setting images.

Figure 10:
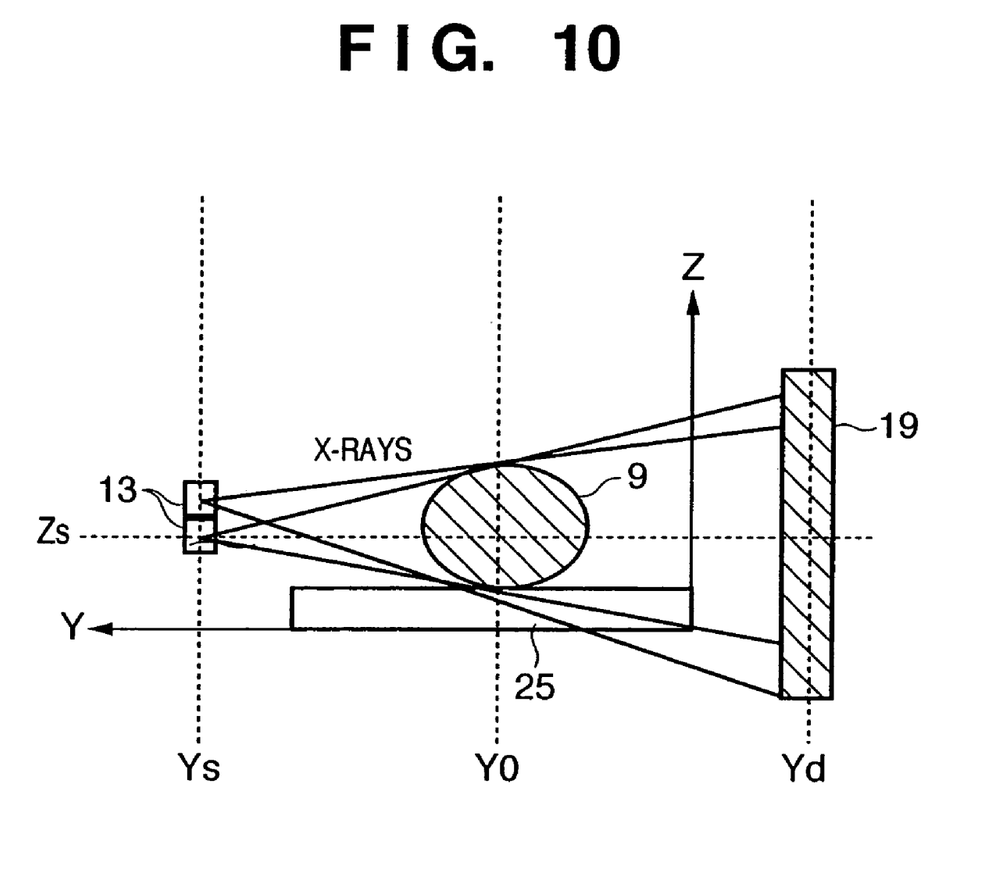
FIG. 10 is a view showing acquisition conditions for a plurality of setting images in the second embodiment.

More specifically, as shown in FIG. 10, by acquiring setting images from two different points in the Z direction, as shown in FIG. 10, a tomosynthesis surface in the Y direction can be set. A display device used for setting allows the technician to stereoscopically see two images by the left and right eyes. That is, the images are displayed upon rotation of 90° on the display screen. There is no need to use a stereoscopic display device such as a liquid crystal shutter in order to express a stereoscopic sense. The persistence of human vision can also be used by switching and displaying setting images at intervals of about 10 ms.

[Other Embodiment]

The present invention incorporates a case wherein programs of software (the tomosynthesis imaging method of the present invention) for implementing the functions of the embodiments described above are directly or remotely supplied to a system or apparatus to cause the computer of the system or apparatus to read out and execute the programs, thereby implementing the functions. In this case, the form of the present invention need not be programs as long as it has the functions of the programs.

The program codes themselves which are installed in the computer to allow the computer to implement the functions/processing of the present invention also realize the present invention. That is, the computer programs themselves, which implement the functions/processing of the present invention, are also incorporated in the claims of the present invention.

In this case, each program may take any form, e.g., an object code, a program executed by an interpreter, and script data supplied to an OS, as long as it has the function of the program.

As a recording medium for supplying the programs, a flexible disk, hard disk, optical disk, magnetooptical disk, MO, CD-ROM, CD-R, CD-RW, magnetic tape, nonvolatile memory card, ROM, DVD (DVD-ROM or DVD-R), or the like can be used.

In addition, methods of supplying the programs include the following. A client computer connects to a home page on the Internet by using a browser to download each computer program of the present invention itself from the home page on the Internet or download a compressed file containing an automatic install function into a recording medium such as a hard disk from the home page. Alternatively, the programs can be supplied by dividing the program codes constituting each program of the present invention into a plurality of files, and downloading the respective files from different home pages. That is, the claims of the present invention also incorporate a WWW server which allows a plurality of users to download program files for causing the computer to execute the functions/processing of the present invention.

In addition, the functions/processing of the present invention can be implemented by encrypting the programs of the present invention, storing the encrypted data in storage media such as CD-ROMs, distributing them to users, allowing users who satisfy a predetermined condition to download key information for decryption from a home page through the Internet, executing the encrypted programs using the key information, and allowing a computer to install the programs.

The functions of the above embodiments are implemented not only when the readout programs are executed by the computer but also when the OS running on the computer performs part or all of actual processing on the basis of the instructions of the programs.

The functions of the above embodiments are also implemented when the programs read out from the storage medium are written in the memory of a function expansion board inserted into the computer or a function expansion unit connected to the computer, and the CPU of the function expansion board or function expansion unit performs part or all of actual processing on the basis of the instructions of the programs.

The present invention is not limited to the above embodiments and various changes and modifications can be made within the spirit and scope of the present invention. Therefore, to apprise the public of the scope of the present invention, the following claims are made.

What is claimed is:

1. An imaging apparatus, comprising:
    an imaging unit constructed to execute imaging of radiation transmitted through a subject and obtain radiographic image data for setting a tomosynthesis surface;
    a tomosynthesis surface setting unit constructed to set the tomosynthesis surface on a basis of the radiographic image data; and
    a tomosynthesis condition setting unit constructed to set a tomosynthesis imaging condition on a basis of the set tomosynthesis surface,
    wherein said tomosynthesis surface setting unit sets a shape of the tomosynthesis surface, and the shape of the tomosynthesis surface includes a flat surface and wherein a curved surface.

2. The apparatus according to claim 1, wherein the radiographic image is obtained by imaging along a direction substantially perpendicular to a moving direction of an X-ray source.

3. The apparatus according to claim 1, wherein the tomosynthesis surface comprises a surface extending along a body axis of the subject.

4. The apparatus according to claim 1, wherein the tomosynthesis imaging condition includes at least one of an X-ray stop condition, an X-ray driving voltage, an X-ray driving current, and a pivoting scanning condition for an X-ray source.

5. The apparatus according to claim 1, wherein the radiographic image data comprises image data taken from at least two orthogonal directions.

6. An imaging method, comprising:
    an imaging step of imaging of radiation transmitted through a subject and obtaining radiographic image data for setting a tomosynthesis surface;
    a tomosynthesis surface setting step of setting the tomosynthesis surface on a basis of the radiographic image data; and
    a tomosynthesis condition setting step of setting a tomosynthesis imaging condition on a basis of the set tomosynthesis surface,
    wherein in said tomosynthesis surface setting step, a shape of the tomosynthesis surface is set, and wherein the shape of the tomosynthesis surface includes a flat surface and a curved surface.

* * * * *